US010628979B2

(12) United States Patent
Stepanek et al.

(10) Patent No.: US 10,628,979 B2
(45) Date of Patent: Apr. 21, 2020

(54) COMPUTER SYSTEM AND METHOD FOR DIAGNOSTIC DATA DISPLAY

(71) Applicant: Mayo Foundation for Medical Education and Research, Rochester, MN (US)

(72) Inventors: Jan Stepanek, Scottsdale, AZ (US); Gaurav N. Pradhan, Fountain Hills, AZ (US); Daniela Cocco, Phoenix, AZ (US); Michael J. Cevette, Scottsdale, AZ (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 78 days.

(21) Appl. No.: 15/517,567

(22) PCT Filed: Nov. 4, 2015

(86) PCT No.: PCT/US2015/059003
§ 371 (c)(1),
(2) Date: Apr. 7, 2017

(87) PCT Pub. No.: WO2016/073582
PCT Pub. Date: May 12, 2016

(65) Prior Publication Data
US 2017/0309048 A1 Oct. 26, 2017

Related U.S. Application Data

(60) Provisional application No. 62/074,932, filed on Nov. 4, 2014.

(51) Int. Cl.
*G06T 11/20* (2006.01)
*G16H 50/20* (2018.01)

(52) U.S. Cl.
CPC ........ *G06T 11/206* (2013.01); *G09G 2380/08* (2013.01); *G16H 50/20* (2018.01)

(58) Field of Classification Search
None
See application file for complete search history.

(56) References Cited

U.S. PATENT DOCUMENTS 5,046,499 A 9/1991 Berger
9,730,582 B1 * 8/2017 Stone ..................... A61B 3/113
(Continued)

FOREIGN PATENT DOCUMENTS

WO 2010037400 A1 4/2010

OTHER PUBLICATIONS

Dicken, V., et al. "Novel CT Data Analysis and Visualization Techniques for Risk Assessment and Planning of Thoracic Surgery in Oncology Patients." International Congress Series, 1281:783-787, 2005.

(Continued)

*Primary Examiner* — Ke Xiao
*Assistant Examiner* — Jed-Justin Imperial (57) ABSTRACT

A method for operating a computer system to generate and display multidimensional data. A set of multidimensional data points and a selected deviation range is received at a processor. The processor processes each data point to determine its value about the selected deviation range. Display data representative of data point indicia of the determined data point values at circumferentially spaced locations and with respect to an origin in a coordinate system is generated and stored by the processor. The data point indicia for the multidimensional data points are at circumferentially spaced locations, and a radial distance of the indicia with respect to (Continued)

the origin represents the determined data point values. A visual display of the display data can be produced on a printer or monitor.

19 Claims, 10 Drawing Sheets

(56) References Cited

U.S. PATENT DOCUMENTS

| | | |
|---|---|---|
| 2005/0008209 A1 | 1/2005 | Matsumoto |
| 2005/0102316 A1 | 5/2005 | Lawson et al. |
| 2006/0045328 A1 | 3/2006 | Jacob et al. |
| 2008/0208027 A1 | 8/2008 | Heaton |
| 2010/0201687 A1 | 8/2010 | Breeuwer et al. |
| 2010/0214297 A1* | 8/2010 | Heidkamp .............. G06T 11/206 345/440 |
| 2013/0268570 A1* | 10/2013 | Koo ........................ G06F 17/18 708/202 |
| 2014/0184608 A1 | 7/2014 | Robb et al. |

OTHER PUBLICATIONS

Harris, Randall, L., Sr., et al. "Analytical Techniques of Pilot Scanning Behavior and Their Application." NASA Technical Paper 2525 19860018448, Jul. 1986, 52 pages.

International Preliminary Report on Patentability issued in PCT/US2015/059003, dated May 18, 2017, 9 pages.

International Search Report and Written Opinion issued in PCT/US2015/059003, dated Mar. 3, 2016, 16 pages.

Korkusuz, Huedayi, et al. "Accuracy of Cardiovascular Magnetic Resonance in Myocarditis: Comparison of MR and Histological Findings in an Animal Model." Journal of Cardiovascular Magnetic Resonance, 12:49, pp. 1-10, 2010.

Misslisch, H., et al. "Neural Constraints on Eye Motion in Human Eye-Head Saccades." J. Neurophysiol., 79:859-869, 1998.

Ren, L., et al. "Proprioceptive Guidance of Saccades in Eye-Hand Coordination." J. Neurophysiol., 96:1464-1477, 2006.

* cited by examiner

COMPUTER SYSTEM AND METHOD FOR DIAGNOSTIC DATA DISPLAY

CROSS REFERENCE TO RELATED APPLICATION

This application is a national phase application of PCT Application No. PCT/US2015/059003, internationally filed on Nov. 4, 2015 and entitled Computer System And Method For Diagnostic Data Display, which claims the benefit of U.S. Provisional Application Ser. No. 62/074,932 filed on Nov. 4, 2014 and entitled Computer System And Method For Diagnostic Data Display, which are both incorporated herein by reference in their entireties and for all purposes.

FIELD OF THE INVENTION

The invention is a computer system and method for generating and displaying medical and other data.

BACKGROUND

Activities such as research in medical and other fields can result in the generation or collection of sets of multidimensional data. Complex data of this type is often processed and displayed in visual form for review and analysis. There remains, however, a continuing need for improved systems and methods for processing and displaying multidimensional data. For example, there is a need for systems and methods that can enhance the visualization of information from the data. In particular, there is a need for systems and methods that enhance a user's ability to gain insight and understanding from the data to facilitate the accurate and efficient interpretation of the data (e.g., for diagnostic decisions).

SUMMARY

Embodiments of the invention include a method for operating a computer system to generate display data representative of a display of multidimensional data. In embodiments, a set of multidimensional data points is received at a processor. The processor processes each data points to determine its value about a deviation range, including optionally a z-vector score, standard deviation, median absolute deviation or cumulative percent. The processor generates and stores display data representative of data point indicia of the determined data point values at circumferentially spaced locations and with respect to an origin in a coordinate system. The data point indicia for the multidimensional data points are at circumferentially spaced locations, and a radial distance of the indicia with respect to the origin represents the determined data point values. Other embodiments include producing a visual display of the generated display data on a monitor or printer.

DESCRIPTION OF THE INVENTION

Introduction and Overview

Embodiments of the invention include computer systems, programmed media and methods to process multidimensional data, generate data representative of visual displays of the data, and to provide visual or graphical displays of the data. These visualization tools enable users to efficiently gain insight from complex multidimensional data. For example, the tools can enhance the users' abilities to understand the data and to facilitate accurate interpretation and diagnostic decisions. The data is transformed into a multidimensional (e.g., 2D) plane, enabling users to interactively discover multivariate relationships among a large number of dimensions. Embodiments of the invention can perform simultaneous analysis of multiple parameters to unveil previously unknown patterns which may lead to a deeper understanding of the underlying phenomena or trends. These embodiments can also provide simplified diagnostic views for users that give them the ability to quickly compare and visualize individual high-dimensional data points with normative samples.

Figure 1:
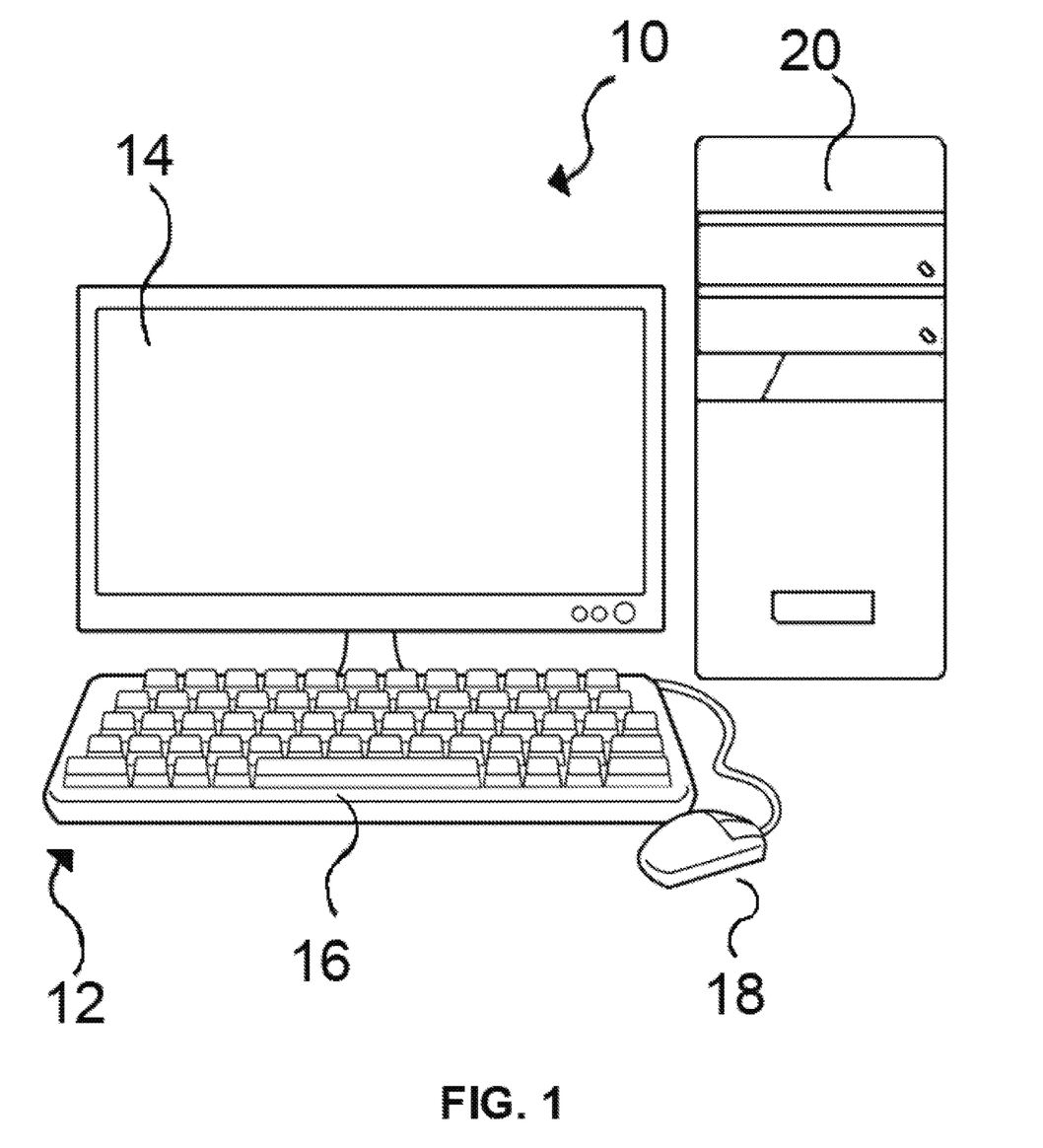
FIG. 1 is a diagrammatic illustration of a computer system that can be used to implement embodiments of the invention.

FIG. 1 is a diagrammatic illustration of a computer system 10 in accordance with embodiments of the invention. As shown, computer system 10 includes a graphical user interface 12 having a monitor 14, keyboard 16 and mouse 18. A processing system 20 that has memory (e.g., ROM and/or RAM, not separately shown) is coupled to the user interface 12. Programs reflecting instructions and algorithms for performing data processing methods in accordance with embodiments of the invention, and data representative of visual displays in accordance with embodiments of the invention, can be stored in the memory. Computer system 10 can be interfaced (e.g., by wireless or wired networks) to other computer or data collection systems (not shown). For example, multidimensional data that is to be processed by computer system 10 can be received over such a network, and data representative of visual displays produced by the computer system can be transferred to other computer systems over such a network. Visual displays in accordance with the invention can be presented on monitor 14 or a printer (not shown). The illustrated embodiment of computer system 10 is shown for purposes of example, and other embodiments of the invention have different or additional components, such as other user interfaces for administrators and providers that use the system, and different or additional memory and database structures.

Figure 2:
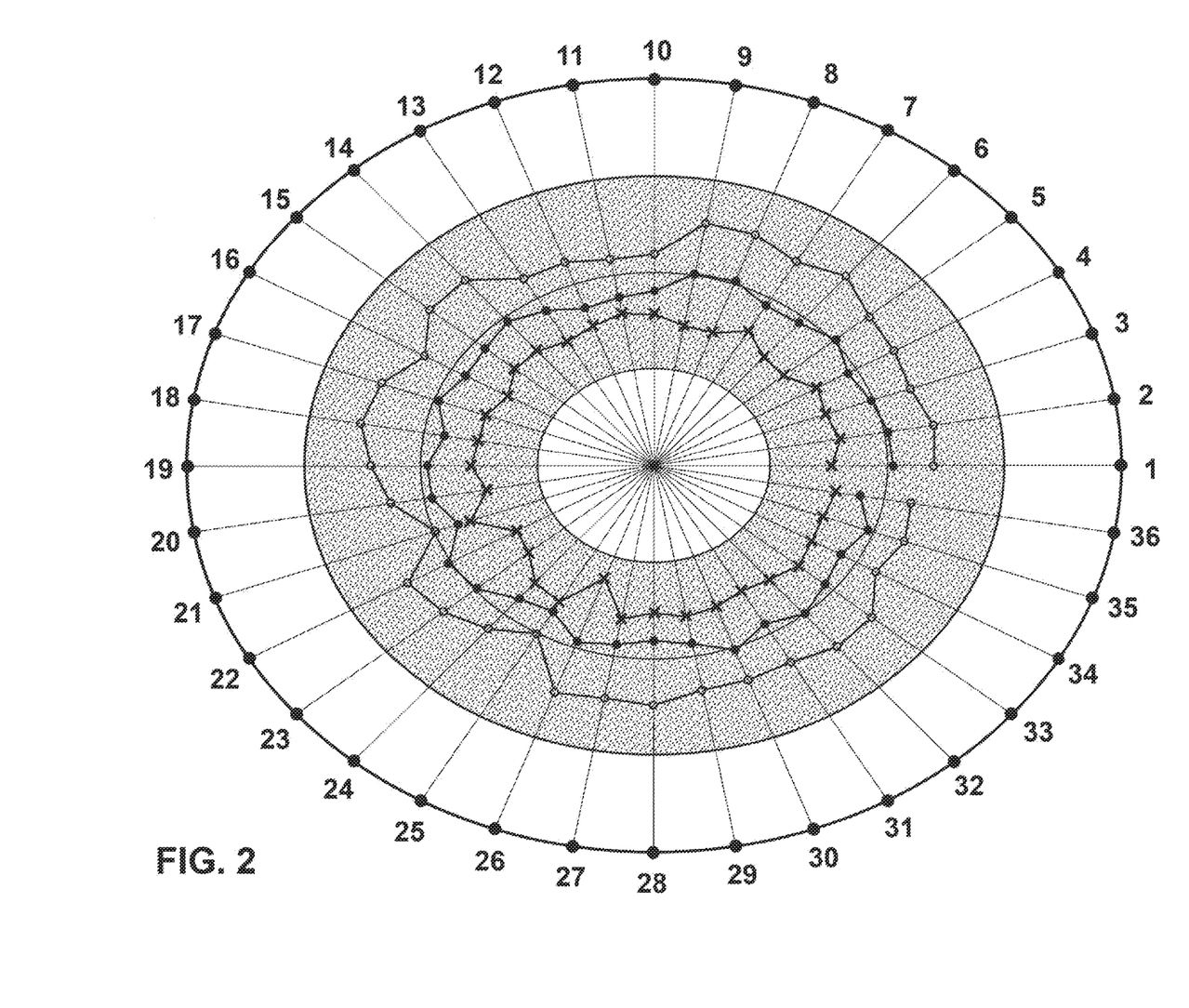
FIG. 2 is an exemplary visual display of a coordinate system and plotted multidimensional data in accordance with embodiments of the invention.

FIG. 2 is an exemplary visual display of a coordinate system including three (3) sets of thirty-six (36) dimension data point indicia in accordance with embodiments of the invention. The data point indicia of the first set are represented by open dots (i.e., "○"), those of the second set by closed dots (i.e., "•"), and those of the third set by the letter "x". As shown, the data point indicia are in the form of a thirty six vertex polygon, where each vertex is circumferentially spaced about an origin, and located on an individual radius of a two-dimensional circumferential construct C such as a circle or oval with having a radius length RL, where:

RL=2×Deviation, and Deviation is a selected number representative of a deviation range. In some embodiments, Deviation is 2-5. The data point indicia for each of the different dimensions is at a different circumferentially spaced location. The location of each data point indicia along the radius length RL represents the value of the data point along the deviation range (e.g., a standard normal distribution in the embodiment shown in FIG. 2). For example, in embodiments where Deviation=3, data points representing values having a standard deviation of −3σ are plotted at the origin (i.e., center of circle C), data points representing values having a standard deviation of +3σ are plotted at the circumference of the circle, and data points representing 0σ values are plotted mid-way between the origin and circumference of the circle. The display shown in FIG. 2 includes a circle illustrating the 0σ coordinates, and shading that represent the range of −1.5σ to +1.5σ coordinates.

General Description

In embodiments of the invention, Y is a set of X N-dimensional data points to be processed and displayed, i.e., $$Y=\{y_x=(y_{x,1}, y_{x,2}, \ldots, y_{x,N}) | 1 \leq x \leq X\}$$

where X is the total number of high-dimensional data points, and N is the dimension of the data or total number of variables.

Along each dimension i, $\bar{y}_i$, $\sigma_i$, and $m_i$ can be the corresponding mean, standard deviation, and median value across X objects, respectively. Hence, the equivalent N-dimensional mean, standard deviation and median vectors are given by, $$\bar{Y}=\{\bar{y}_1, \bar{y}_2, \ldots, \bar{y}_N\}$$

$$\sigma=\{\sigma_1, \sigma_2, \ldots, \sigma_N\}$$

$$M=\{m_1, m_2, \ldots, m_N\}$$

Methods in accordance with the invention transform the N-dimensional data point into an N-vertex polygon, where each vertex is located on the individual radius of a 2-D circle with a radius length of 2*Deviation, where Deviation is a value that can be set by the user, and is between 2 to 5 in some embodiments.

Figure 3:
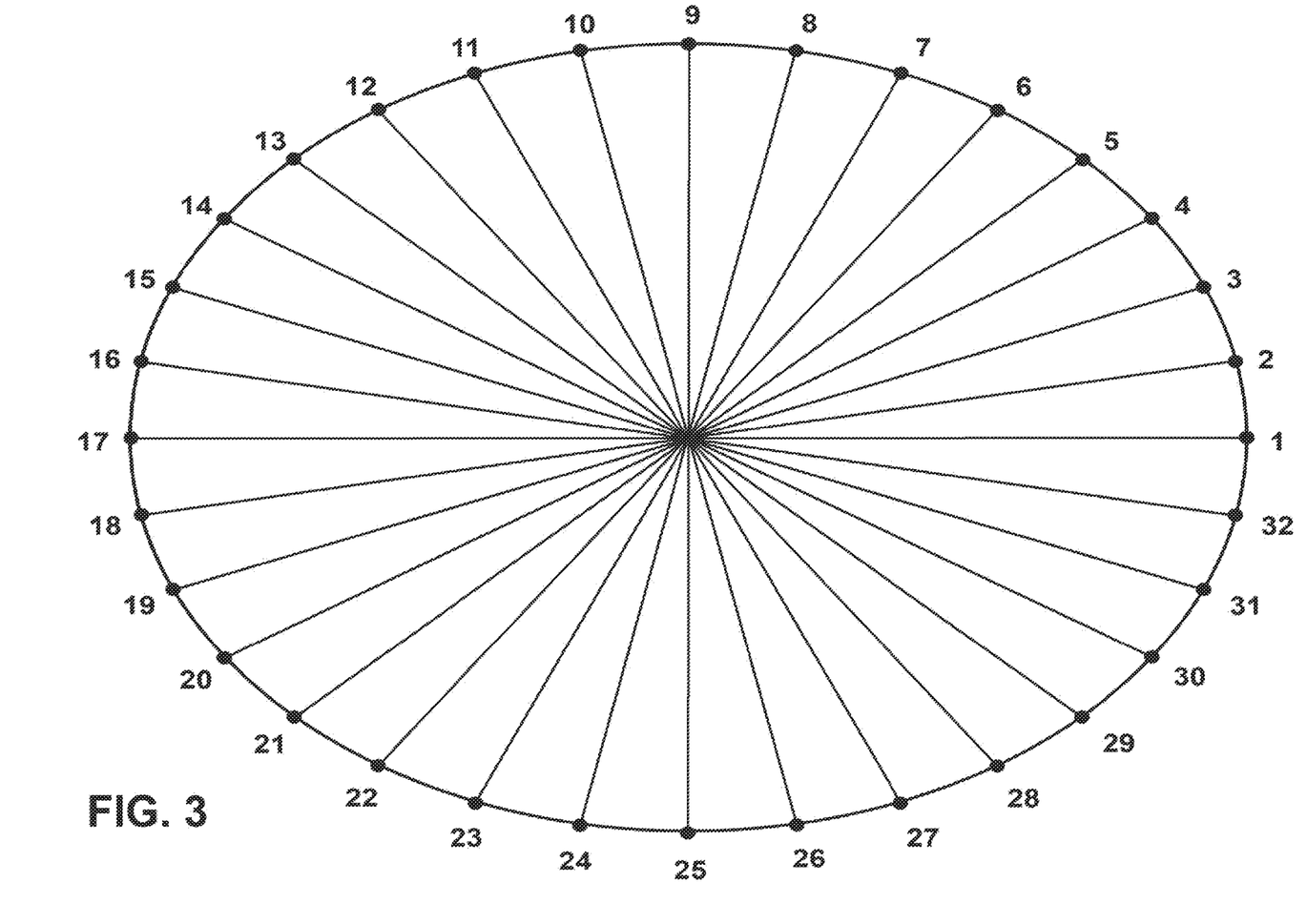
FIG. 3 is an illustration of a coordinate system in accordance with embodiments of the invention for the display of thirty-two dimension data sets.

In the exemplary coordinate system shown in FIG. 3, each radius corresponds to one of the N variables (for e.g. N=32 in FIG. 3). The angular distance between each neighboring variable on the circumference of the circle is given by $$\frac{(2*\pi)}{N}.$$

Assuming without the loss of generality that the center of the circle is at origin (0,0), the location of the $i^{th}$ radius is given as, $$L_i = \left\{ \left( r*\cos\left((i-1)*\frac{(2*\pi)}{N}\right), r*\sin\left((i-1)*\frac{(2*\pi)}{N}\right) \right) \middle| 1 \leq i \leq N \right\}$$

where r is the radius of the circle equal to 2*Deviation. The method transforms the $n^{th}$ radius into a standard normal distribution for the corresponding $n^{th}$ variable. The standard normal distribution for the $n^{th}$ variable is derived from normal distribution $N(\bar{y}_n, \sigma_n)$ by standardizing the values of $n^{th}$ variable. In other words, calculating z-scores of value b for variable n, which is given by $$z = \frac{b - \bar{y}_n}{\sigma_n}.$$

The center end of the radius corresponds to −Deviation*$\sigma_n$ and $n^{th}$ point on the circumference corresponds to Deviation*$\sigma_n$. The value of Deviation is user-defined (e.g., as per the requirement of associate research).

Figure 4:
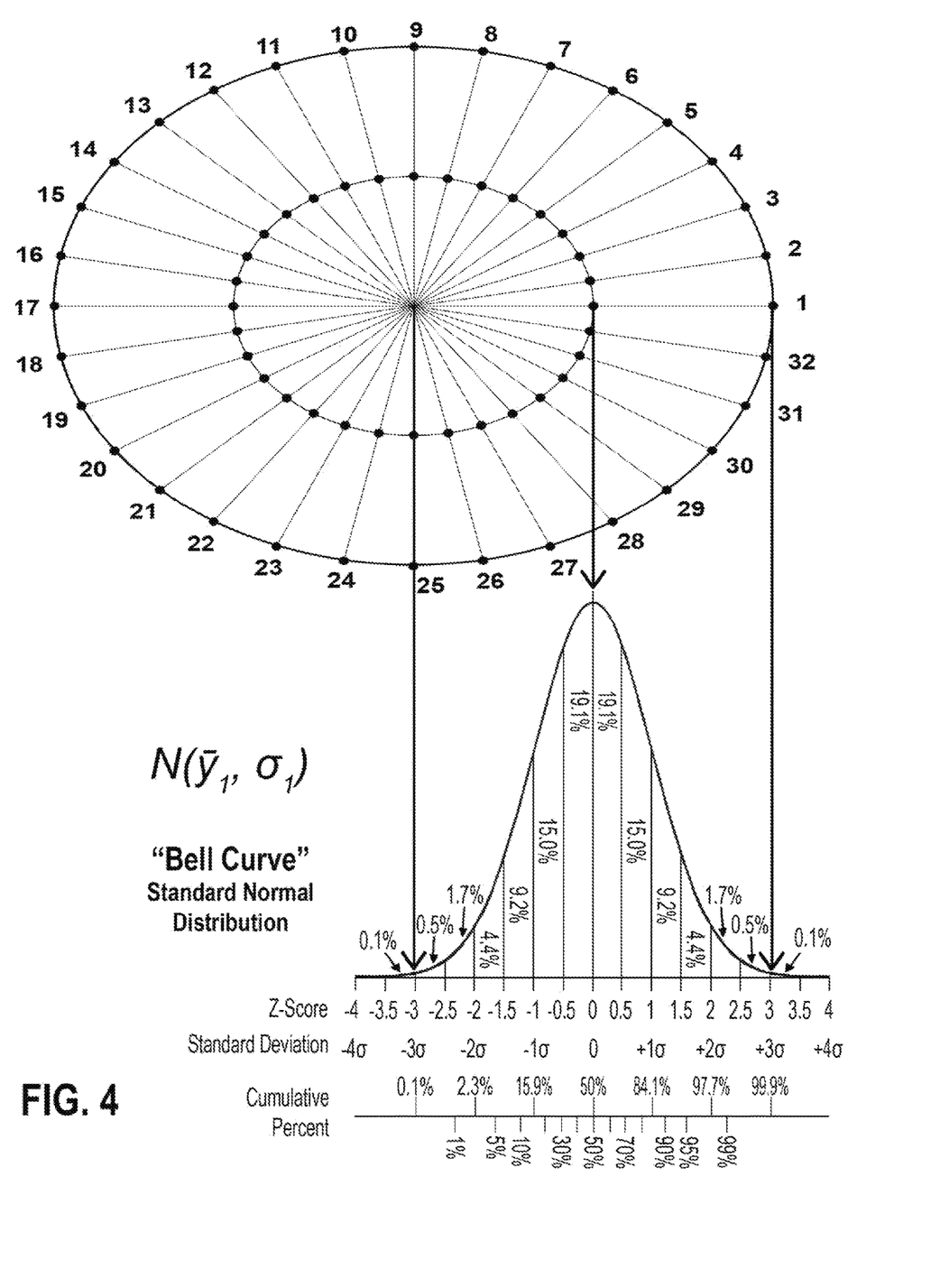
FIG. 4 is an illustration of the coordinate system shown in FIG. 3, showing how data plotted on the coordinate system represents values over a standard normal deviation from $-3\sigma$ to $+3\sigma$.
Figure 5:
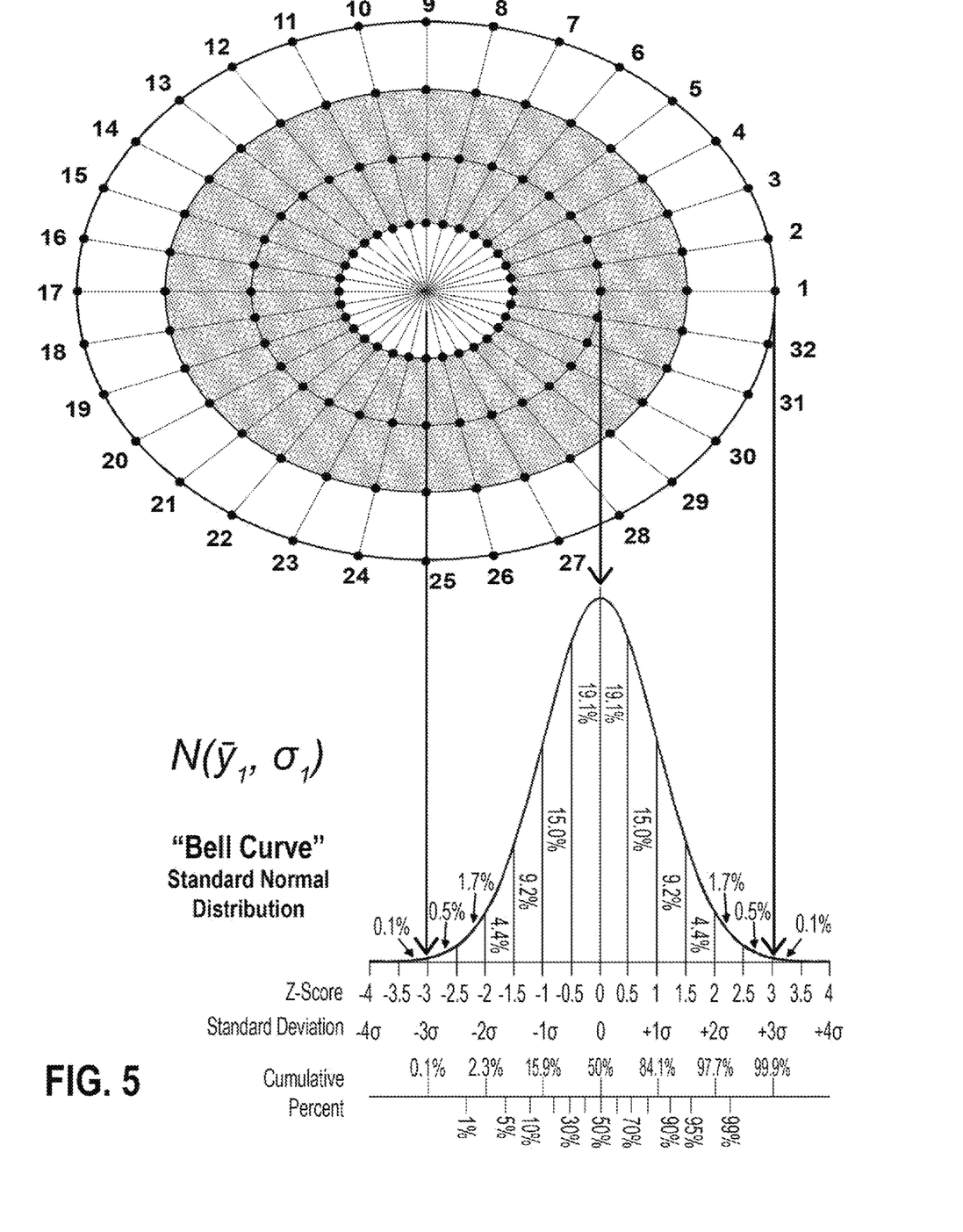
FIG. 5 is an illustration of the coordinate system shown in FIG. 4, with the addition of indicators of data values in the range of $-1.5\sigma$ to $+1.5\sigma$.

FIG. 4 is an illustration of a coordinate system shown in FIG. 3, when Deviation is set to 3. As represented by the bell curve, data plotted on the coordinate system of FIG. 4 will represent values over a standard normal deviation from of −3σ to +3σ. As is also shown in FIG. 4, as all the variables are transformed to their standard normal distribution on their respective radii, joining the standardized means (i.e. z=0) of all variables gives a concentric circle on the coordinate system. Similarly, other standard deviation values and ranges can be indicated on the coordinate system. FIG. 5, for example, shows the coordinate system of FIG. 4 with indicators such as shading that represents the values for any $n^{th}$ variable below +1.5$\sigma_n$ and above −1.5$\sigma_n$ (i.e. within 1.5 standard deviations of the means). The value 1.5 in connection with the coordinate system shown in FIG. 5 is user-defined and exemplary only, and an end-user can choose to display indicia representing any value between 0 and Deviation depending on an application. If for any variable, values go beyond this range (i.e. z>+1.5), then the corresponding point for that variable may be plotted out of the illustrated coordinate system.

In the embodiments described above, the data display is driven by the mean and standard deviation of the variables. However, the mean and standard deviations may be strongly impacted by outliers and hence models using mean as a central tendency indicator may be unlikely to detect outliers in samples. Accordingly, other embodiments of the invention use median as a measure of central tendency as opposed to mean. And instead of standard deviation, other embodiments use the median absolute deviation (MAD) for $n^{th}$ variable, which can be represented as follows:

$$MAD_n = b*\{\text{Median } (|y_{x,n} - m_n|) | 1 \leq x \leq X\}$$

where b=1/Q(0.75), and Q(0.75) is the 0.75 quantile of the underlying distribution. In case of normal distribution, 1/Q (0.75) is 1.4826. The standardized z-score of value b for variable n is then given by:

$$z = \frac{b - m_n}{MAD_n}.$$

Visual analytics can be represented through two types of models in accordance with the invention:
1. ($\overline{Y}$, $\sigma$)—"mean-standard deviation", or
2. (M, MAD)—"median-median absolute deviation".

Processing Algorithm

The following is a pseudo-code algorithm that can be implemented by embodiments of the invention (e.g., by computer system 10) to visualize (e.g., generate and plot) the N-dimensional data points on coordinate systems as described above:
1. Given N-dimensional data point, D={$d_1, d_2, \ldots, d_N$}. The radius of the coordinate system is set to 2*Deviation.
2. Convert the N-dimensional data point into z-vector,
   a. For ($\overline{Y}$, $\sigma$), $$z_{d_i} = \frac{d_i - \overline{y}_i}{\sigma_i} \bigg| 1 \le i \le N$$

b. For (M, MAD), $$z_{d_i} = \frac{d_i - m_i}{MAD_i} \bigg| 1 \le i \le N$$

3. Limiting the values of z-scores within [−Deviation, +Deviation] to fit in the coordinate system, IF $z_{d_i}$>Deviation, then $z_{d_i}$=Deviation. OR IF$z_{d_i}$<−Deviation then $z_{d_i}$=−Deviation 4. Scaling the Z-scores to fit the coordinate system, $zs_{d_i} = z_{d_i} + $Deviation$ | 1 \le i \le N$ 5. Plotting the scaled z-score on the respective radius of the coordinate system, assuming the center of the coordinate system is at origin (e.g., (0,0)), $$L_{d_i} = \left\{ \left( zs_{d_i} * \cos\left((i-1) * \frac{(2*\pi)}{N}\right), zs_{d_i} * \sin\left((i-1) * \frac{(2*\pi)}{N}\right) \right) \bigg| 1 \le i \le N \right\}$$

Example

Case Study I: Acute Hypoxia Effects on Oculometrics

Figure 6:
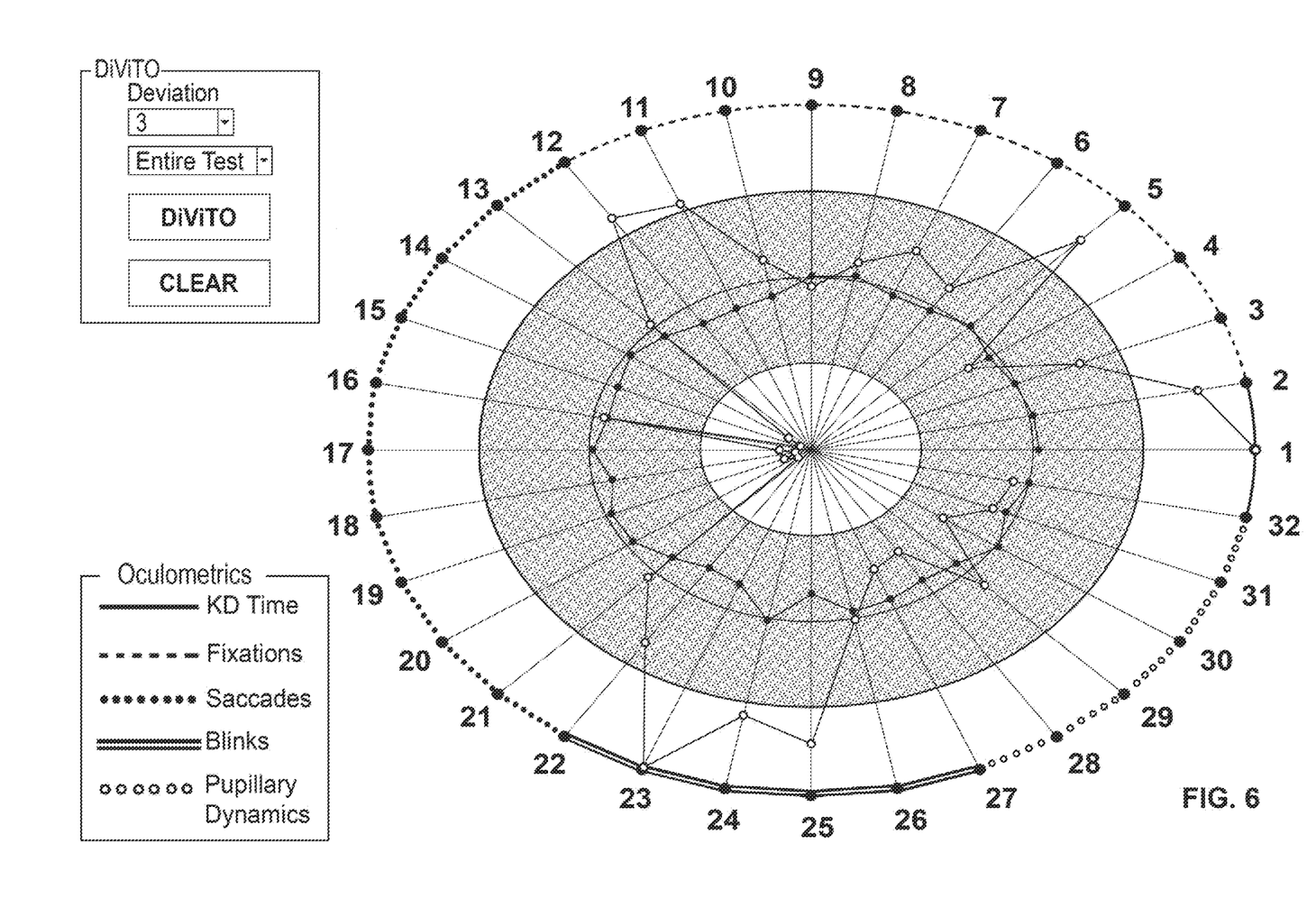
FIG. 6 is an example of a display of two sets of multidimensional data in accordance with embodiments of the invention.

Thirty two (32) oculometric features are measured by using non-contact, non-invasive eye-tracking technology during the performance of computerized neuro-cognitive tests. All oculometric features are categorized mainly into four categories and can be grouped accordingly: fixations, saccades, blinks and pupillary dynamics. FIG. 6 shows the visualization of oculometric features for one subject performing a neuro-cognitive test in hypoxia (data points of curve formed by open dots (i.e., "○"). The curve formed by closed dot data points (i.e., "•") represents the average curve of oculometric features across twenty subjects at normal baseline. It is evident from the display of FIG. 6 that the test time (variable #1), fluctuation in fixation time (variable #5), many saccadic features mainly including average saccadic lengths (variable #14), saccadic velocities (variable #19), and then blink rate (variable #23) and blink durations (variable #24) of the subject are significantly affected by hypoxia. This display also shows how hidden trends of oculometrics in hypoxic environments can be unveiled by the invention.

Figure 7:
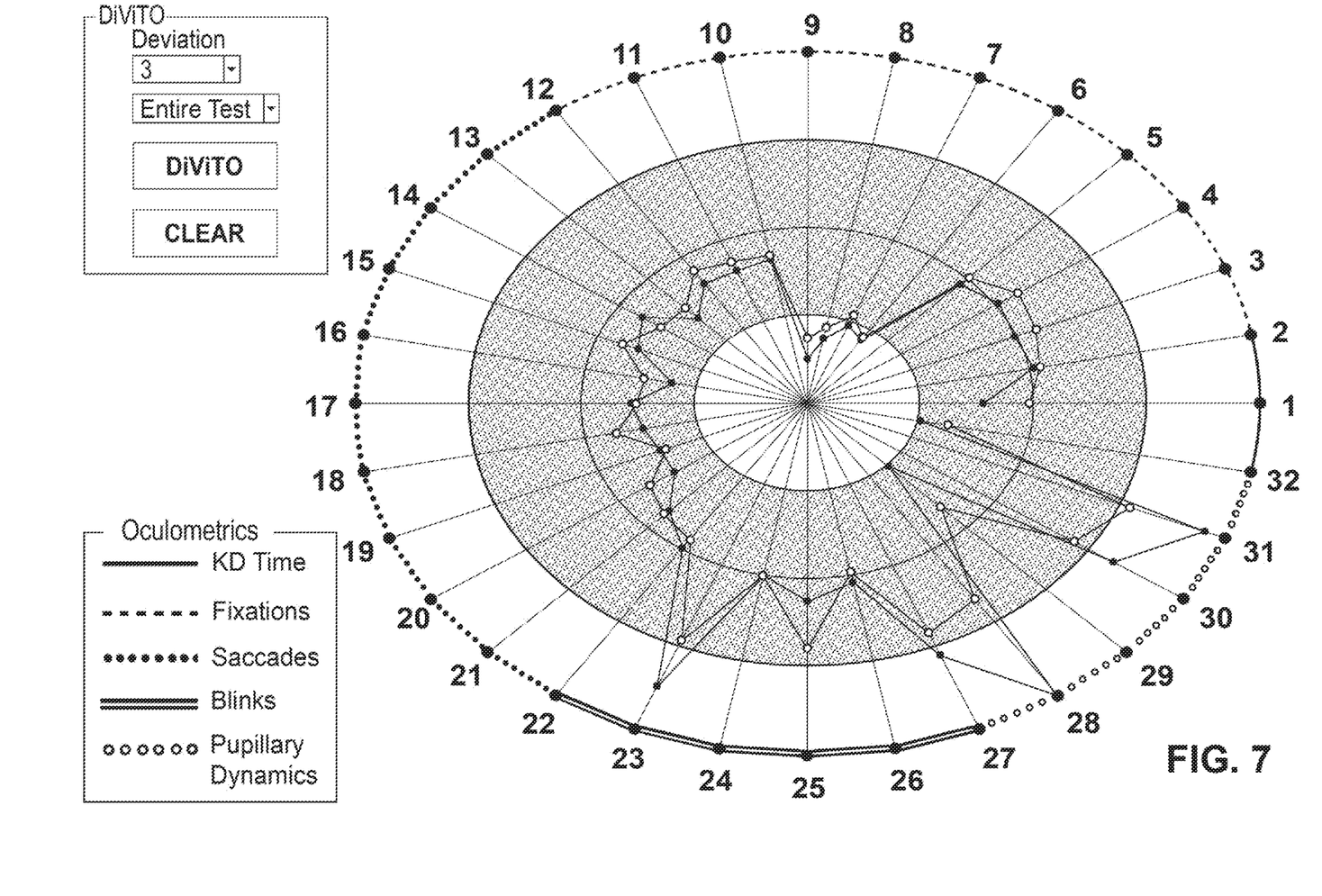
FIG. 7 is another example of a display of two sets of multidimensional data in accordance with embodiments of the invention.

FIG. 7 is an illustration of a display showing a comparison of oculometric features for the same subject (from which data shown in FIG. 6 was collected) but different hypoxic conditions: normoxic baseline (curve formed by open dots) and hypoxia (curve formed by closed dots). From this display it is very that the blink rate (variable #23), fluctuation in left (variable #28) and right (variable #31) pupil size are affected in hypoxia for this individual subject.

Example

Case Study II: Acute Hypoxia Effects on Cardiovascular Parameters

Embodiments of the invention have been applied to visualize complete hemodynamic physiological data that includes five different sets of cardiovascular parameters as follows:
1. Twelve beat-to-beat (BTB) cardiovascular parameters: RR-interval (RRI), Heart Rate, Systolic Blood Pressure (sBP), Diastolic Blood Pressure (dBP), Mean Arterial Blood Pressure, Stoke Volume, Stroke Index, Cardiac Output, Cardiac Index, Total Peripheral Resistance, Total Peripheral Resistance Index, Maximum rise in Pulse Pressure.
2. Six Transthoracic Bioimpedance Cardiography (ICG) parameters: End-diastolic Index (EDI), IC, Acceleration Contractibility Index (ACI), Left Ventricular Work Index (LVWI), Left Ventricular Ejection Time (LVET), and Thoracic Fluid Content (TFC).
3. Eight autonomic heart rate variability (HRV) parameters: RRI Low Frequency normalized unit (LFnu-RRI), RRI High Frequency normalized unit (HFnu-RRI), RRI Very Low Frequency (VLF-RRI), RRI Low Frequency (LF-RRI), RRI High Frequency (HF-RRI), RRI Power Spectral Density (PSD-RRI), RRI Ratio of Low Frequency to High Frequency (LF/HF-RRI), and Ratio of Low Frequency to High Frequency (LF/HF)
4. Eight parameters related to the frequency analysis of systolic blood pressure: sBP Low Frequency normalized unit (LFnu-sBP), sBP High Frequency normalized unit (HFnu-sBP), sBP Very Low Frequency (VLF-sBP), sBP Low Frequency (LF-sBP), sBP High Frequency (HF-sBP), sBP Power Spectral Density (PSD-sBP), sBP Ratio of Low Frequency to High Frequency (LF/HF-sBP), and Ratio of Low Frequency to High Frequency (LF/HF).
5. Eight parameters related to the frequency analysis of diastolic blood pressure: dBP Low Frequency normalized unit (LFnu-dBP), dBP High Frequency normalized unit (HFnu-dBP), dBP Very Low Frequency (VLF-dBP), dBP Low Frequency (LF-dBP), dBP High Frequency (HF-dBP), dBP Power Spectral Density (PSDdBP), dBP Ratio of Low Frequency to High Frequency (LF/HF-dBP), and Ratio of Low Frequency to High Frequency (LF/HF).

Figure 8:
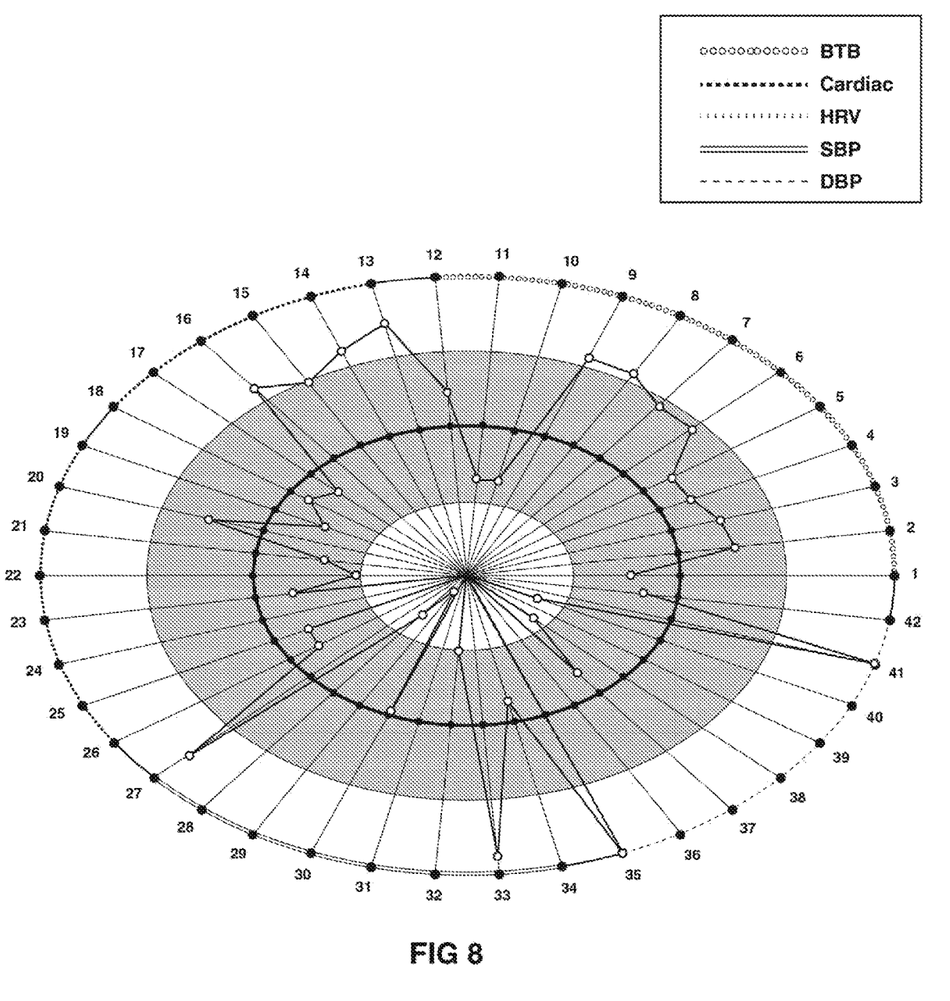
FIG. 8 is an illustration of a coordinate system in accordance with embodiments of the invention for the display of forty-two dimension data sets.

Overall, all 42 parameters from 5 different sets of hemodynamic systems were combined and displayed to provide complete diagnostic view and interactivity to discover multivariate relationships between multiple physiological data sets. FIG. 8 shows the individualized cardiovascular performance in hypoxic environment. The shaded zone represents the normal range of all 42 parameters for the given subject. The curve in the center of the shaded zone is the baseline measurement and another curve represents the cardiovascular performance of the same subject after breathing five minutes of hypoxic gas (8% $O_2$+balance $N_2$) which is equivalent to breathing at 22000 feet. The generated display clearly shows the cardiovascular performance difference of the same individual at high altitude as compared to the baseline. This kind of individualized display can be used in research as well as diagnostic purpose to evaluate the physiological performance not only in high altitudes but also in other challenging environments such as, but not limited to, space, deep water diving, during surgical operations etc. Similar to this case study, displays generated in accordance with embodiments of the invention can visualize the lab results of all medical tests conducted during a medical exam. Thus, displays in accordance with the invention have the potential to visualize an entire Electronic Medical Record (EMR) of a patient. This will facilitate all physicians to have one unified view of all labs to diagnose the medical problem and effectively provide medical treatment based on the results of all lab tests.

Example

Case Study III: Early Warning Signs during Hyperventilation

Figure 9:
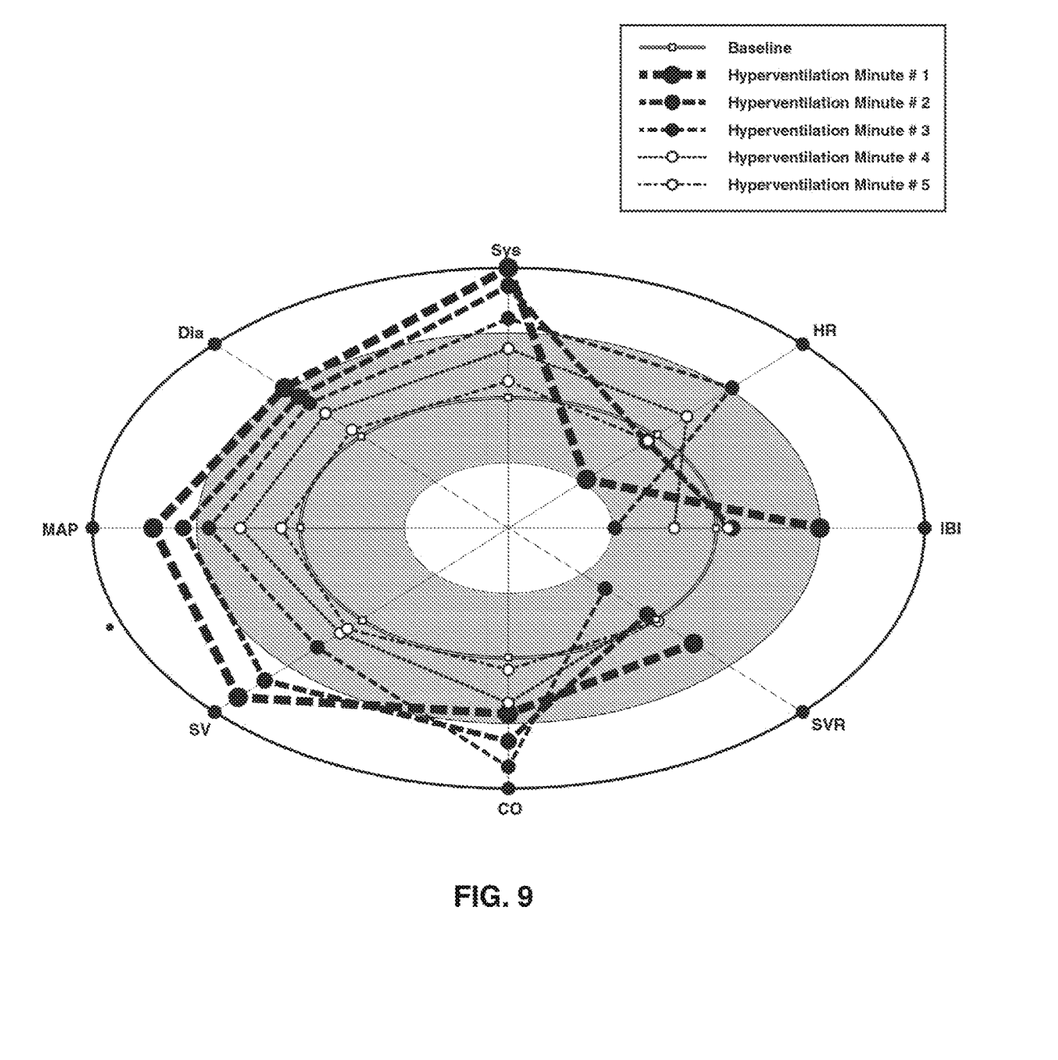
FIG. 9 is an illustration of a display of multiple sets of multidimensional data on a common coordinate system in accordance with embodiments of the invention, where each set represents data at different times (i.e., temporally spaced data sets).

Embodiments of the invention have been adapted to continuously monitor multiple physiological parameters as shown in FIG. 9. FIG. 9 shows the adaptation of a display that monitors the changes of eight hemodynamic parameters during hyperventilation, where each set of multidimensional data is presented on a common coordinate system. A curve in the middle of the shaded zone corresponds to the baseline of the subject before hyperventilation. The data represented by one curve corresponds to the hemodynamic performance of the subject after 1 minute of hyperventilation, which is clearly outside the shaded zone for most of the parameters. It should be noted that at 1 minute of hyperventilation even though hemodynamic parameters are significantly different from their respective baselines the subject did not perceive any symptoms. In this particular situation, if one continues to hyperventilate further, he/she can later experience common symptoms of hyperventilation such as dizziness, lightheadedness, tingling sensation, cognitive impairment and in worst case loss of consciousness. In this specific case example, based on the interpretive visualization power of displays in accordance with embodiments of the invention, a warning sign can be generated after 1 minute of hyperventilation to alert an individual about hyperventilation. As a result, the subject tries to recover, which can be observed in the display by curves showing the status of hemodynamic parameters at $2^{nd}$ and $3^{rd}$ minute of hyperventilation coming close to the shaded zone. At $4^{th}$ and $5^{th}$ minute, the hemodynamic parameters are close to the baseline showing the complete recovery from hyperventilation. Thus, displays in accordance with embodiments of the invention can be integrated in real-time systems that continuously monitor multiple physiological parameters, and can provide holistic view of all monitored parameters in a single snapshot to assist diagnostic decisions and provide early warning signs.

Figure 10:
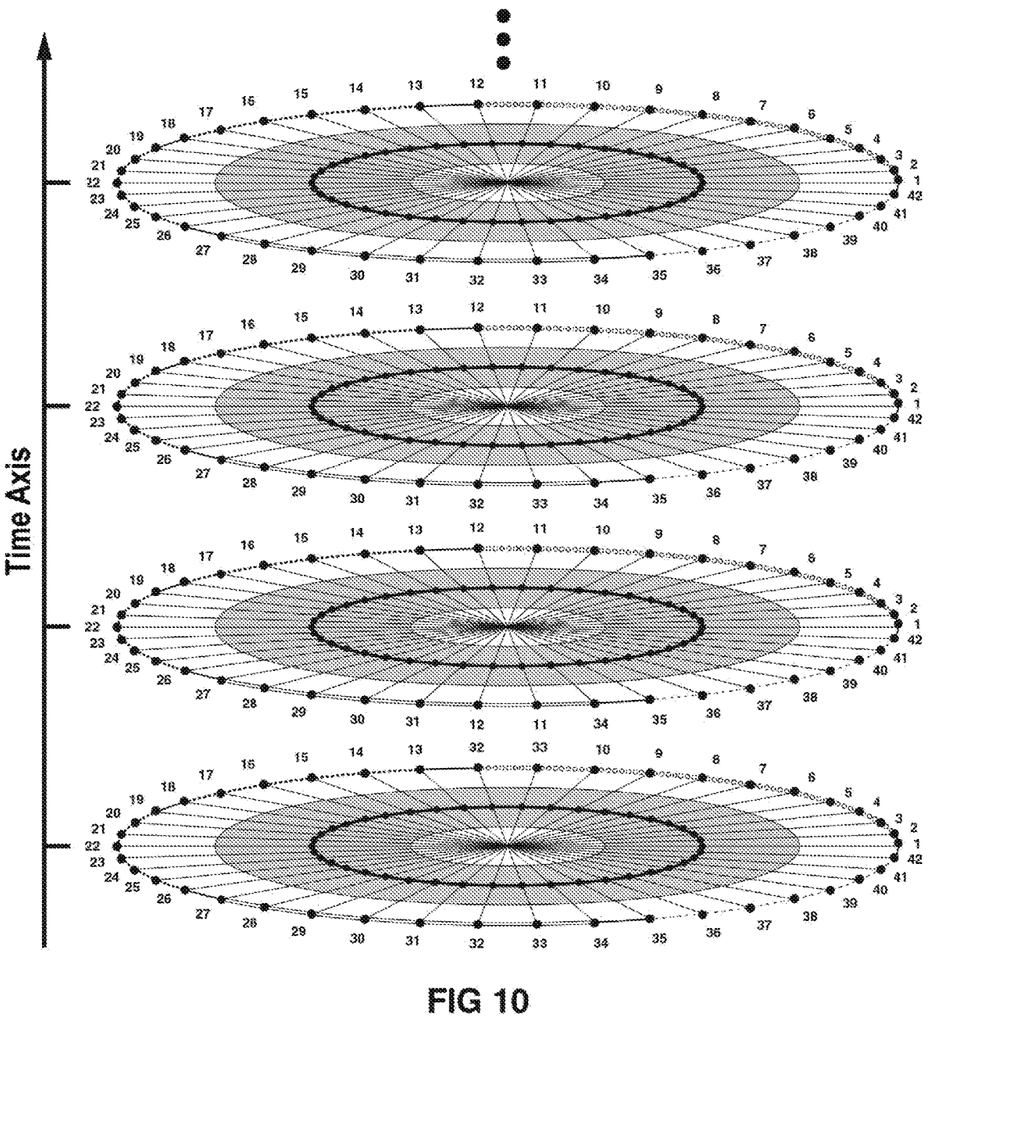
FIG. 10 is an illustration of a display of multidimensional data sets on separate coordinate systems at spaced apart locations with respect to a time axis in a common image or display frame in accordance with embodiments of the invention.

Embodiments of the invention can be extended to additional domains. For example, displays in accordance with embodiments of the invention can be presented in 3D. FIG. 10 is an example of a 3D display that visualizes multiple displays along time axes. Sets of multidimensional data are presented in the multiple displays having separate coordinate systems in a common image or display frame. The time axes can also represent number of subjects where each display corresponds to each subject to monitor multiple subjects at the same time.

Displays in accordance with the invention can be presented in a dynamic or video domain. For example, the continuous monitoring of oculometric performance during the parachute flight from high altitude (e.g., 30000 feet) to the ground level can be presented by a sequence of one or more displays over time, with each sequential display labeled to identify features of the displayed data such as the altitude at which the data was taken. The displayed curves corresponding to high altitudes (e.g., the curves presented during the earlier portions of the sequence) may show significant deviation (e.g., outside the shaded zone) indicating significant changes in the oculometric performance due to hypoxia. In later-displayed curves corresponding to data taken at lower altitudes and as the altitude drops towards the ground level, the oculometric performance may be mainly in the shaded zone indicating return to the normal baseline.

Although the present invention has been described with reference to preferred embodiments, those of ordinary skill in the art will recognize that changes can be made in form and detail without departing from the spirit and scope of the invention. For example, although FIGS. 6 and 7 illustrate displays of oculometric data, the invention is not so limited. Other types of data can be processed and displayed in accordance with other embodiments of the invention.

The invention claimed is:

1. A method for operating a computer system to generate display data representative of a display of multidimensional data, comprising:
receiving a set of multidimensional data points at a processor;
receiving information representative of a user-selected deviation range for the display;
processing each data point based on the user-selected deviation range to determine a deviation value representing its value about the deviation range by the processor, including processing the data points as a function of the mean and standard deviation of the data points to produce mean-standard deviation values, and processing the data points as a function of the median and median absolute deviation of the data points to produce median-median absolute deviation values; and
generating and storing by the processor display data representative of data point indicia of the determined mean-standard deviation values and the median-median absolute deviation values at circumferentially spaced locations and with respect to an origin in a coordinate system, wherein the data point indicia for the multidimensional data points are at circumferentially spaced locations, and a radial distance of the indicia with respect to the origin represents the determined deviation values.

2. The method of claim 1 and further including producing a visual display of the generated display data on a monitor or printer.

3. The method of claim 1 wherein generating display data includes generating data representative of the data point indicia within a radial distance range of two times the user-selected deviation range.

4. The method of claim 1 wherein generating display data further includes generating data representative of indicia of a predetermined range and deviation within the deviation range, and including highlighting a portion of the deviation range.

5. The method of claim 4 and further including producing a visual display of the generated display data on a monitor or printer.

6. The method of claim 1 for generating display data for more than one set of multidimensional data.

7. The method of claim 6 and further including generating display data for a plurality of displays with respect to a time axis in a common display frame.

8. The method of claim 7 and further including producing a visual display of the generated display data on a monitor or printer.

9. The method of claim 6 wherein each set of the more than one set of multidimensional data is a set representative of data at different times.

10. The method of claim 9 wherein generating the display data includes generating display data representative of each of the more than one set of multidimensional data on a common coordinate system.

11. The method of claim 10 and further including producing a visual display of the generated display data on a monitor or printer.

12. The method of claim 9 wherein generating the display data includes generating display data representative of each of the more than one set of multidimensional data on separate coordinate systems for sequential display.

13. The method of claim 12 and further including producing a visual video display of the generated display data on a monitor.

14. The method of claim 1 for generating display data for oculometric features.

15. The method of claim 1 and further including processing the determined data point values to limit the mean-standard deviation values and the median-median absolute deviation values within a predetermined range, including the deviation range.

16. The method of claim 1 and further including processing the determined mean-standard deviation values and the median-median absolute deviation values to scale the values.

17. The method of claim 1 and further including generating indicia grouping two or more of the dimensions.

18. A computer system configured to perform the method of claim 1.

19. Program media having non-transitory stored instructions for performing the method of claim 1.

* * * * *